(12) United States Patent
Fristrom

(10) Patent No.: US 10,755,739 B1
(45) Date of Patent: Aug. 25, 2020

(54) REMOTE RAILWAY CROSSING PROGRAMMABLE DEVICE AND METHODS THEREOF

(71) Applicant: John Fristrom, Jacksonville, FL (US)

(72) Inventor: John Fristrom, Jacksonville, FL (US)

(*) Notice: Subject to any disclaimer, the term of this patent is extended or adjusted under 35 U.S.C. 154(b) by 372 days.

(21) Appl. No.: 15/814,692

(22) Filed: Nov. 16, 2017

Related U.S. Application Data

(60) Provisional application No. 62/440,480, filed on Dec. 30, 2016.

(51) Int. Cl.
| | |
|---|---|
| *G11B 19/08* | (2006.01) |
| *G11B 19/16* | (2006.01) |
| *B61L 29/30* | (2006.01) |
| *B61L 23/04* | (2006.01) |
| *B61L 27/00* | (2006.01) |

(52) U.S. Cl.
CPC ............ *G11B 19/08* (2013.01); *B61L 23/041* (2013.01); *B61L 29/30* (2013.01); *G11B 19/16* (2013.01); *B61L 27/0088* (2013.01)

(58) Field of Classification Search
CPC ....... G11B 19/08; G11B 19/16; B61L 23/041; B61L 29/30
USPC ...................................................... 246/473.1
See application file for complete search history.

(56) References Cited

U.S. PATENT DOCUMENTS

| | | | | |
|---|---|---|---|---|
| 6,985,071 | B1* | 1/2006 | Tanaka | G11B 19/08 340/309.16 |
| 7,441,727 | B2* | 10/2008 | Sharkey | B61L 29/30 246/114 R |
| 2005/0075764 | A1* | 4/2005 | Horst | B60R 25/25 701/19 |
| 2007/0221791 | A1* | 9/2007 | Voelk | G06Q 10/047 246/1 R |
| 2013/0256466 | A1* | 10/2013 | Carlson | B61L 5/00 246/218 |
| 2015/0291193 | A1* | 10/2015 | Perras | B61L 25/025 246/122 R |

OTHER PUBLICATIONS

UTE Safety Solutions, Inc: Smart Jumper Model 100-1200 brochure, entire document.

\* cited by examiner

*Primary Examiner* — Jason C Smith
(74) *Attorney, Agent, or Firm* — Allen Dyer Doppelt & Gilchrist, PA

(57) ABSTRACT

A railway crossing programmable device includes a communication module in signal communication with a central server for authentication of a user to use the programmable device to modify the railway system circuit. The programmable device further includes a circuit modification module configured for electrical coupling to a railway system circuit for modifying an electrical connection of the railway system circuit in a programmed manner. The programmable device further includes a user interface configured to receive user data and display output information related to at least one of a user, a device, and a circuit modification.

17 Claims, 7 Drawing Sheets

REMOTE RAILWAY CROSSING PROGRAMMABLE DEVICE AND METHODS THEREOF

CROSS-REFERENCE TO RELATED APPLICATION

The present application claims the benefit of U.S. Provisional Patent Application Ser. No. 62/440,480, filed on Dec. 30, 2016, the contents of which are herein incorporated by reference in their entirety.

FIELD OF THE INVENTION

The present invention relates to a programmable electronic device, and more particularly, to a programmable device that carries out operational control of a railway crossing system, railway signal system, or other safety critical applications where impairment to safe operation of such systems can have undesired outcomes.

BACKGROUND OF THE INVENTION

Railroad companies are often responsible for maintaining electromechanical features of rail crossing stations, including rail crossing traffic systems and related equipment. Railroad maintenance personnel or contractors can be responsible for human errors that arise in the context of testing, maintaining or diagnosing functions of rail crossing traffic systems or other life critical systems or equipment, leading to significant undesirable outcomes. For example, it is customary to change or disable the rail crossing traffic close to a track maintenance site, and by human error the rail crossing traffic system might not be reset or enabled after maintenance is complete. This could result in vehicle collisions, or personal injury. These and other shortcomings are addressed in the present disclosure.

SUMMARY OF THE INVENTION

It is to be understood that both the following general description and the following detailed description are exemplary and explanatory only and are not as restrictive as claimed. The present invention is related to remote railway crossing programmable device and methods thereof. A railway crossing programmable device includes a communication module in signal communication with a central server for authentication of a user to use the programmable device to modify the railway system circuit. The programmable device further includes a circuit modification module configured for electrical coupling to a railway system circuit for modifying an electrical connection of the railway system circuit in a programmed manner. The programmable device further includes a user interface configured to receive user data and display output information related to at least one of a user, a device, and a circuit modification.

According to another embodiment of the present invention, a method of modifying a railway circuit using a programmable device includes coupling a plurality of electrodes of the programmable device to correspondent maintenance terminals of the railway circuit intended to be modified. A user authentication information is inputted via a user interface of the programmable device. A request code for modification of the railway circuit is generated. An authorization code is received upon a third party verification. A circuit modification is set via the programmable device.

These and other objects, aspects and advantages of the present invention will be better appreciated in view of the drawings and the following detailed description of preferred embodiments.

DETAILED DESCRIPTION OF PREFERRED EMBODIMENTS

Before the present methods and systems are disclosed and described, it is to be understood that the methods and systems are not limited to specific methods, specific components, or particular implementations. It is also to be understood that the terminology used herein is for the purpose of describing particular embodiments only and is not intended to be limiting.

As will be appreciated by one of ordinary skill in the art, the methods and systems of concern here may take the form of a computer program product on a computer-readable storage medium having computer-readable program instructions embodied in the storage medium. Any suitable computer-readable storage medium may be utilized, including hard disks, CD-ROMs, optical storage devices, and magnetic storage devices. The computer program instructions may also be stored in a computer-readable memory that can direct a computer or other programmable data processing apparatus to function in a particular manner, such that the instructions stored in the computer-readable memory produce computer-readable instructions for implementing certain functions. The computer program instructions may also be loaded onto a computer or other programmable data processing apparatus to cause a series of operational steps to be performed on the computer or other programmable apparatus to produce a computer-implemented process.

Figure 1:
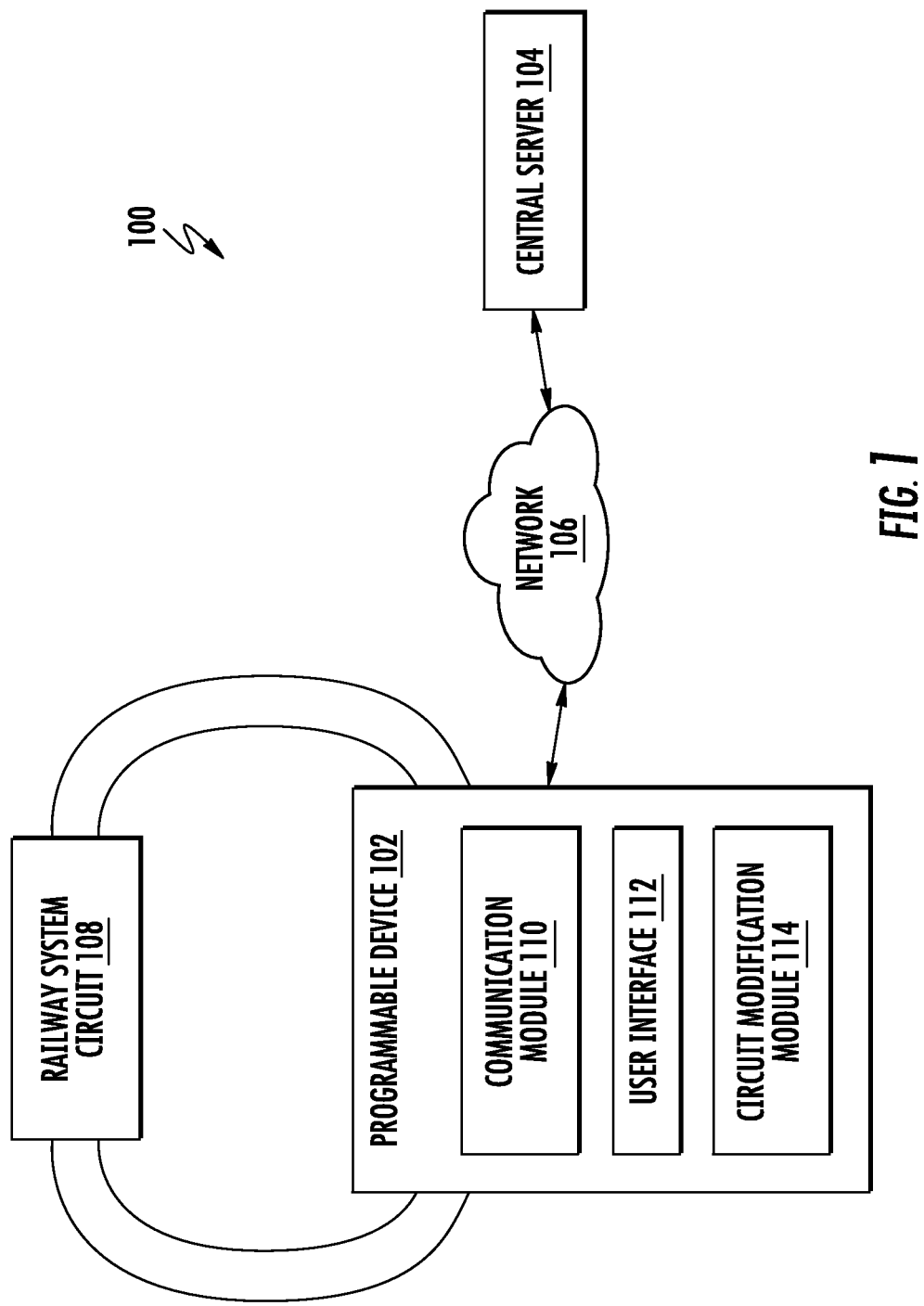
FIG. 1 is a block diagram of an exemplary system in which a remote programmable device can operate, according to one embodiment of the present invention.

FIG. 1 illustrates various aspects of an exemplary system 100 in which the present methods and systems can operate. One skilled in the art will appreciate that a functional description is provided herein and that the respective functions can be performed by software, hardware, or a combination of software and hardware.

The exemplary system 100 includes a remote programmable device 102 configured to communicate with the central server 104 via a network 106. The programmable device 102 is configured for electrical coupling to a railway system circuit 108 and for modifying (e.g., disabling) the electrical connection of the railway system circuit 108 in a programmed manner. The programmable device 102 is configured such that the modification (e.g., disablement) of the railway crossing system circuit 108 can only be activated via user authentication from the central server 104 (e.g., a third party server). The central server 104 allows the programmable device 102 to interact with remote resources, such as data, devices, and files.

The programmable device 102 includes a communication module 110 in signal communication with the central server 104 for authentication of a user to use the programmable device 102 to modify a railway system circuit 108. As an example, the communication module 110 can include a wireless transceiver, a connector to the Ethernet a cellular transceiver, a telephone connector, a modem, and the like, to communicate with the central server 104. The central server 104 can communicate with the communication module 110 via a variety of transmission paths, including wireless links (e.g., radio frequency, satellite, Bluetooth) and/or physical links (e.g., fiber optic cable, coaxial cable, ethernet cable) capable of carrying communications, media content, and the like. The central server 104 can be in communication with the communication module 110 via a private and/or public network, such as the Internet or a local area network.

The programmable device 102 also includes a user interface 112 to receive user information and display output information related to at least one of a user, a device, and a circuit modification. As an example, user authentication information includes user login information, user name, user number, user password, and the like. As another example, device information includes a device identification number. As another example, circuit modification information includes a request code, an authentication code, and the like. The user interface 112 can also be configured to change (e.g., extend, reduce) the time and/or duration of the modification before or after modification is activated. The user interface 112 can be configured to receive manual command and/or voice command from the user. Once a modification is activated, the date, time, circuit status related to the modification can be displayed on an output panel of user interface 112 in real-time. The circuit modification will be automatically restored upon expiration of the entered amount of time at the designated date. The user interface 112 can also be configured to select or specify a specific jumper circuit to be modified. The user interface 112 can also be configured to set specific durations of modification for each of a plurality of jumper circuits.

The programmable device 102 further includes a circuit modification module 114 configured for modifying (e.g., disabling) an electrical connection of the railway system circuit 108 in a programmed manner.

In use, the programmable device 102 is coupled to the corresponding test maintenance terminals of an equipment or railway circuit (e.g., railway circuit 108) intended to be affected. A user can verify that the correct time and date are set in the programmable device 102. Once the time and date are verified by the user, a date, time and duration of modification is then set via the user interface 112. A request code is then generated by the programmable device 102 and transmitted to a third party (e.g., central server 104) for verification. A third party (e.g., central server 104) ensures that the programmed data and internal clock of the programmable device 102 are accurate. After validation, the third party (e.g., central server 104) will then generate an authorization code and transmit the authorization code to the user. The user will in turn enter the authorization code into the programmable device 102. Once the authorization code is entered, the programmable device 102 will modify electrical connectivity across its connected circuit or equipment for the time period specified by programming.

Figure 2:
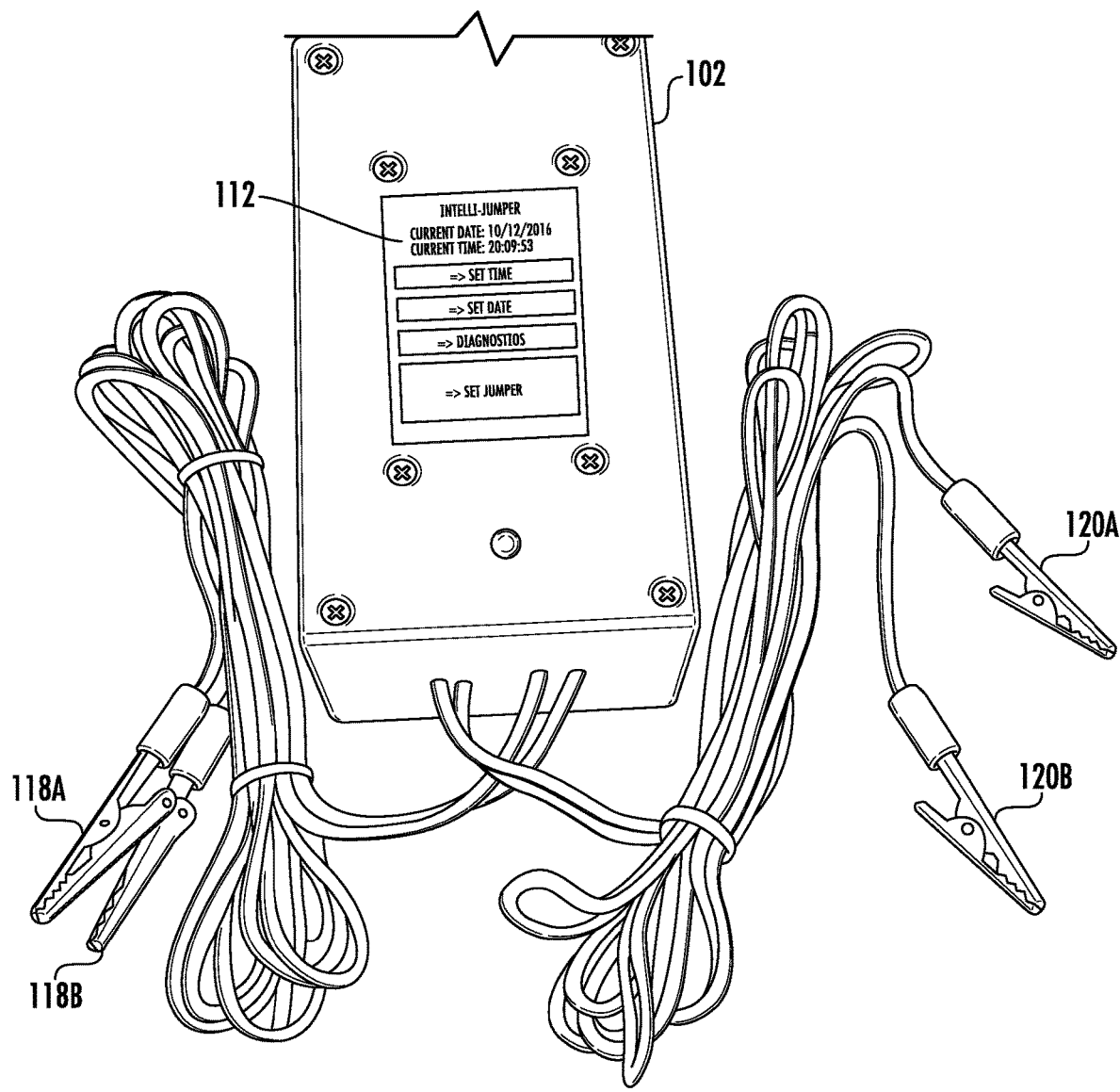
FIG. 2 is a perspective view of an exemplary remote programmable device, according to one embodiment of the present invention.

Referring to FIG. 2, an exemplary programmable device 102 is a portable device that can be hand-held or worn or carried in a pocket. The programmable device 102 can be powered by one or more rechargeable batteries. The programmable device 102 can be charged with a typical cell phone charger. In use, a plurality of electrodes pairs (e.g., 118A and 120A, 118B and 120B) of the programmable device 102 are coupled to the correspondent maintenance terminals of an equipment or circuit intended to be affected. The time, date, request code, authorization code related to a circuit modification can be specified, verified, and/or displayed on the user interface 112 of the programmable device 102.

Figure 3:
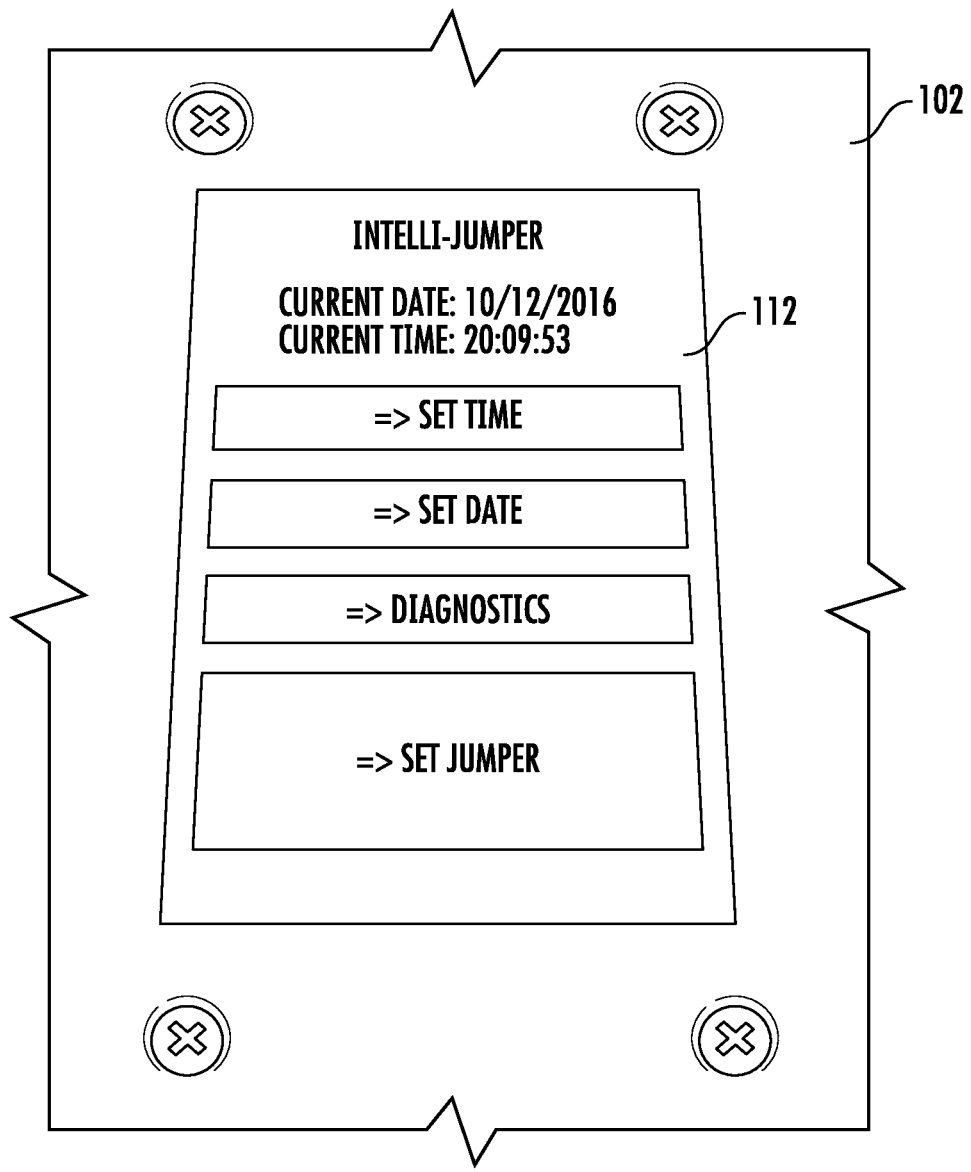
FIG. 3 is a user interface screen of the programmable device of FIG. 2.
Figure 4:
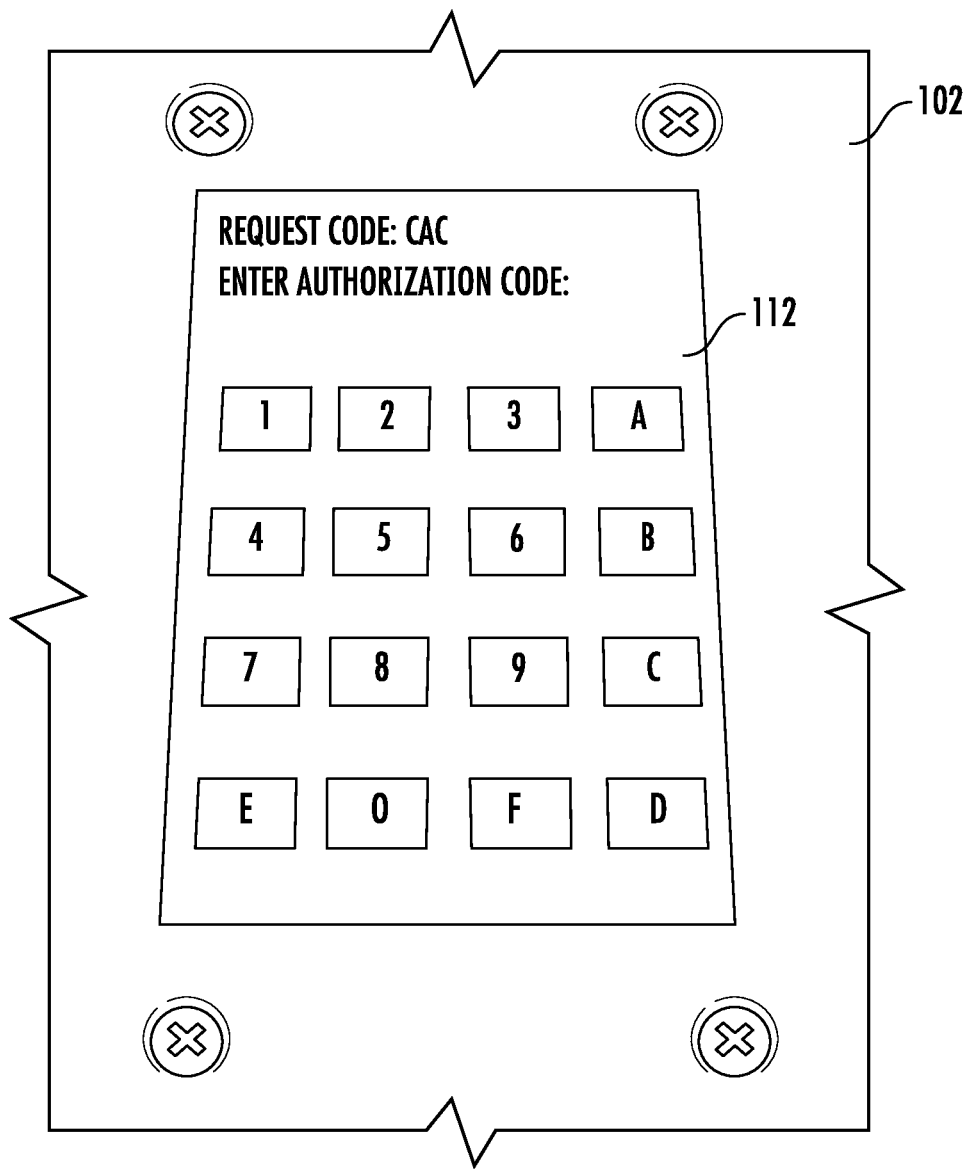
FIG. 4 is another user interface screen of the programmable device of FIG. 2.
Figure 5:
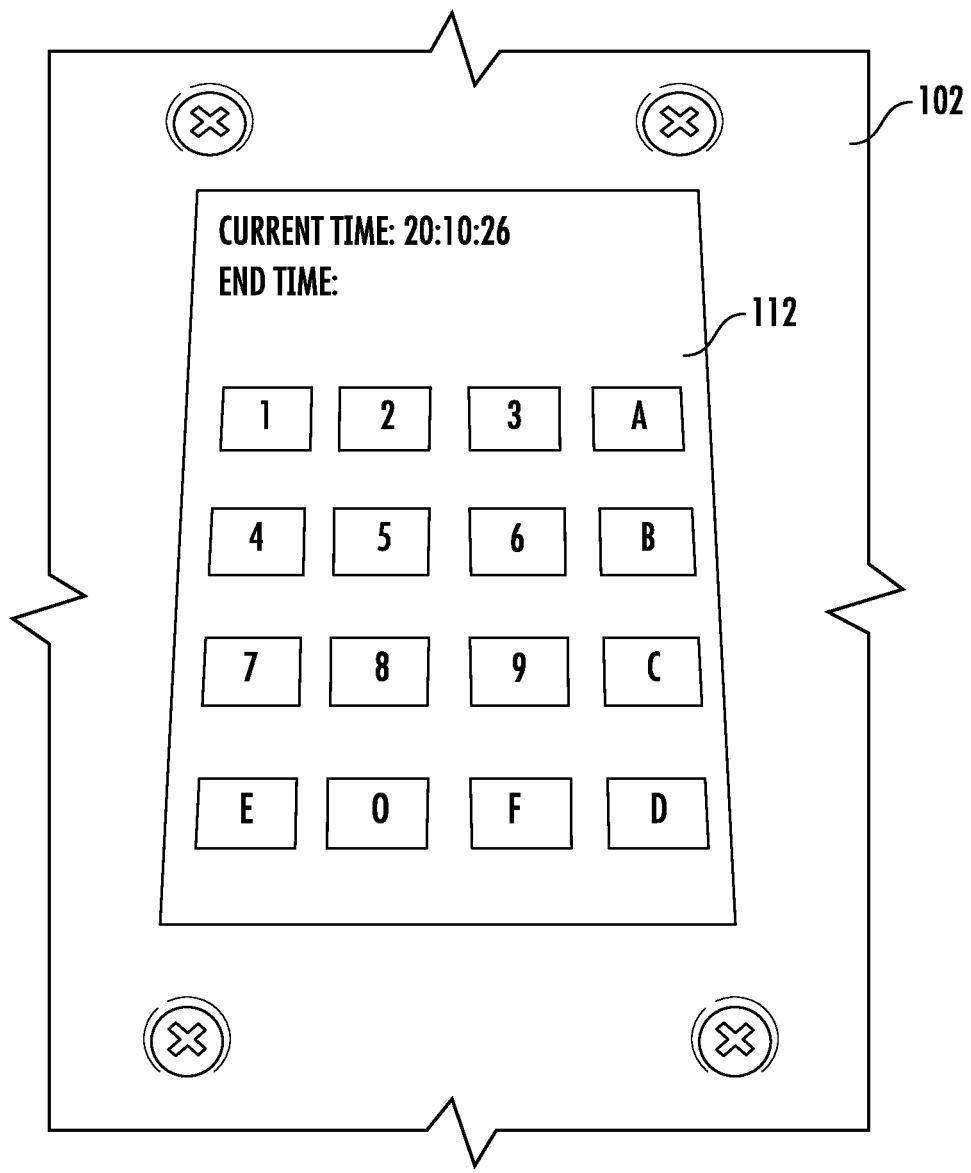
FIG. 5 is another user interface screen of the programmable device of FIG. 2.
Figure 6:
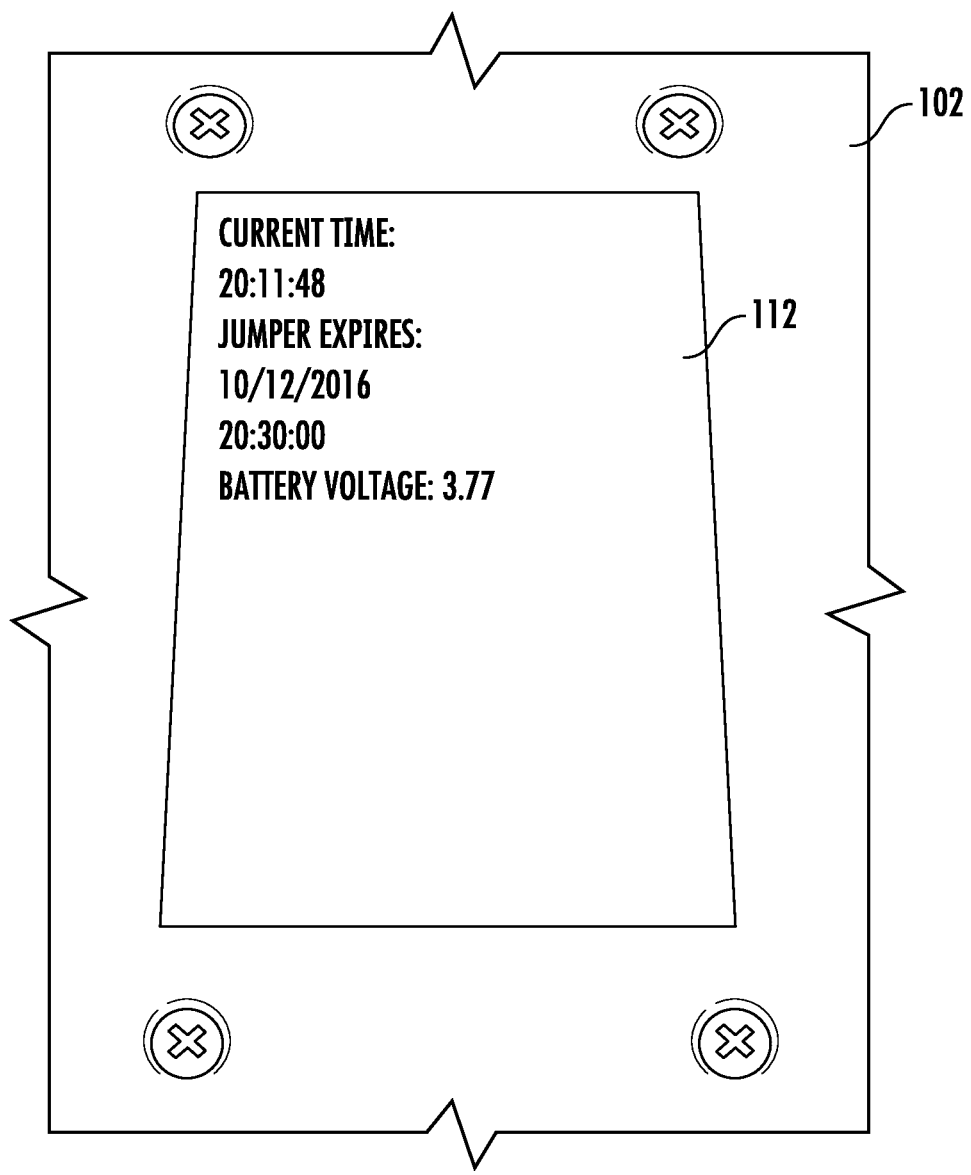
FIG. 6 is another user interface screen of the remote programmable device of FIG. 2.

Referring to FIGS. 3-6, the user interface 112 of the programmable device 102 includes a plurality of screens designed for input and/or output user information, device information, request code, authorization code, date and time (e.g., staring time, end time, remaining time), and the like, related to circuit modification. For example, FIG. 3 shows a user interface 112 screen displaying fields for setting time and date, activating a diagnostic function, and setting modification function of a jumper circuit. FIG. 4 shows a user interface 112 screen displaying a request code and a keypad for entering an authorization code. FIG. 5 shows a user interface 112 screen displaying current time and a keypad for entering an end time associated with a circuit modification. FIG. 6 shows the user interface 112 screen displaying current time, circuit modification expiration time, and battery voltage after the modification is activated.

Figure 7:
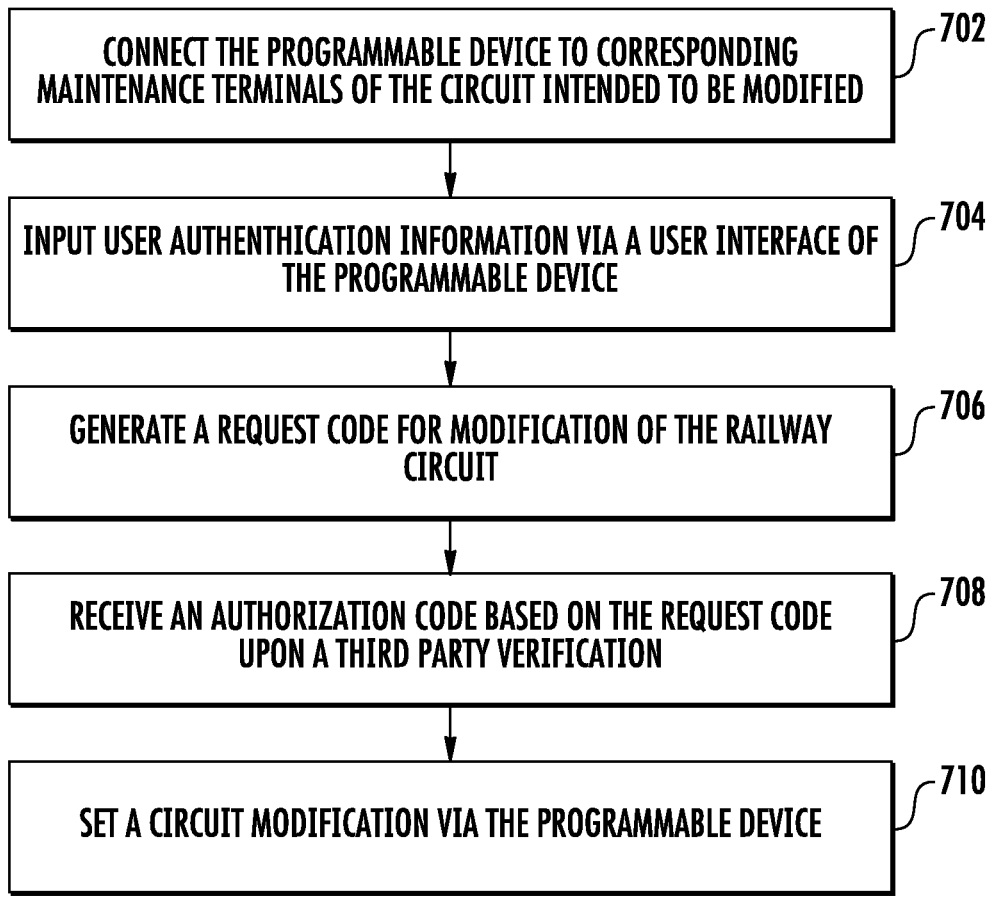
FIG. 7 is a flow diagram of an exemplary method of using the remote programmable device.

FIG. 7 is a flow diagram illustrating an exemplary method for using the programmable device 102 to modify a railway crossing traffic circuit or equipment.

At step 702, the programmable device 102 is connected to corresponding maintenance terminals of a railway circuit or equipment (e.g., jumper circuit 108) intended to be modified.

At step 704, a user and/or the programmable device is authenticated via the central server 104. For example, a user can input user and/device information (e.g., user name, user number, device number) via the user interface 112 for user authentication. In addition, a user is required to verify that correct time and date is set in the programmable device 102.

At step 706, a request code is generated by the programmable device 102 and transmitted to a third party (e.g., central server 104) once the time and date are verified, user and/or device is authenticated and/or authorized. The request code can contain information associated to time, date and duration of a requested modification. The third party ensure programmed data and internal clock of the programmable device 102 is accurate upon receiving the request code.

At step 708, after receiving the request code and validated by the third party, the third party (e.g., central server 104) will then generate an authorization code and transmit the generated authorization code to the user (e.g., user's smart phone) and/or the programmable device 102. The user will in turn enter the authorization code into the programmable device 102.

At step 710, once the authorization code is input into the programmable device 102, the programmable device 102 will modify electrical connectivity across its connected circuit or equipment for the specified time period in which it was programmed. This process and the programmable device 102 ensure that an authorized user and/or an authorized device is programming the maintenance event as intended, reducing the possibility of human error and/or limiting the severity of negative outcomes.

The authorization code can be a variant of the request code. For example, the request code can be a function (e.g., sum) of modification duration data and the value of the identification number of programmable device 102. The authorization code is a modulus result of the modification duration data and the device identification number in hexadecimal format.

It should be mentioned that the methodological steps outlined above do not necessarily have to be executed in a specific order. For example, the programmable device 102 can be connected to a jumper circuit after a user is authorized to program the circuit modification.

While the methods and systems have been described in connection with preferred embodiments and specific examples, it is not intended that the scope be limited to the particular embodiments set forth, as the embodiments herein are intended in all respects to be illustrative rather than restrictive. The device can also be used in other commercial and industrial applications—both within and beyond the railroad industry—where the described functionality would be advantageous.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only.

What is claimed is:

1. A railway crossing programmable device comprising:
   a communication module in signal communication with a central server for authentication of a user to use the programmable device to modify a railway system circuit;
   a circuit modification module including a plurality of electrodes configured for electrical coupling to maintenance terminals of a railway system circuit for modifying an electrical connection of the railway system circuit in a programmed manner; and
   a user interface configured to receive and display information related to at least one of a user, a programmable device, and a circuit modification;
   wherein the circuit modification module is configured to set a specific jumper circuit, and then disable the jumper circuit after a predetermined duration.

2. The programmable device of claim 1, wherein information related to a user includes at least one of user login identification number, user name, user number, user password, and an authentication code.

3. The programmable device of claim 1, wherein information related to a device includes a device identification number.

4. The programmable device of claim 1, wherein information related to a circuit modification includes at least one of an authorization code, a request code, and circuit status of a railway system circuit.

5. The programmable device of claim 4, wherein the authorization code is a variant of the request code.

6. The programmable device of claim 1, wherein the user interface is configured to receive manual input from the user.

7. The programmable device of claim 1, wherein the user interface is configured to receive a voice command from the user.

8. The programmable device of claim 1, wherein the communication module is in signal communication with the central server via a wireless connection.

9. The programmable device of claim 8, wherein the communication module includes at least one of a wireless transceiver, a cable connector, a cellular transceiver, a telephone connector, and a modem.

10. A method of modifying a railway circuit using a programmable device comprising:
    coupling a plurality of electrodes of the programmable device to correspondent maintenance terminals of a railway circuit intended to be modified;
    inputting user authentication information via a user interface of the programmable device;
    generating a request code for modification of the railway circuit;
    receiving an authorization code based on the request code upon a third party verification; and
    setting a circuit modification via the programmable device.

11. The method of claim 10, further comprising transmitting generated request code to a remote central server for the third party verification.

12. The method of claim 10, further comprising conducting a self-diagnostic procedure prior to performing the circuit modification.

13. The method of claim 10, wherein setting the circuit modification includes specifying a starting time and ending time of the circuit modification.

14. The method of claim 10, further comprising verifying current time and date in the programmable device.

15. The method of claim 10, wherein the authorization code is a variant of the request code.

16. The method of claim 10, wherein at least one of the request code and the authorization code is a function of circuit modification duration data and identification number of programmable device.

17. The method of claim 10, further comprising automatically disabling the circuit modification at a predetermined time.

* * * * *